US005679640A

United States Patent [19]

Gaeta et al.

[11] Patent Number: 5,679,640

[45] Date of Patent: Oct. 21, 1997

[54] IMMUNOSUPPRESSANT PEPTIDES

[75] Inventors: Federico C. A. Gaeta, La Jolla; Michael F. Powell, San Francisco; Howard M. Grey; Alessandro D. Sette, both of La Jolla; Thomas S. Arrhenius, San Diego, all of Calif.

[73] Assignees: Cytel Corporation, San Diego, Calif.; Sandoz Ltd., Basel, Switzerland

[21] Appl. No.: 400,781

[22] Filed: Mar. 8, 1995

Related U.S. Application Data

[63] Continuation of Ser. No. 143,973, Oct. 27, 1993, abandoned, which is a continuation of Ser. No. 654,482, Feb. 12, 1991, abandoned.

[51] Int. Cl.$^6$ .......................... A61K 38/00; A61K 38/02; C07K 5/00; C07K 7/00

[52] U.S. Cl. .................................. 514/14; 514/15; 514/13

[58] Field of Search .................................. 514/13, 14, 15; 530/326, 327, 328

[56] References Cited

U.S. PATENT DOCUMENTS 4,826,765 5/1989 Greene et al. .

FOREIGN PATENT DOCUMENTS 9008161 7/1990 WIPO .............................. C07L 7/08

OTHER PUBLICATIONS

Urban et al., Cell, vol. 59, pp. 257–271, 1989.

Wraith et al., Cell, vol. 59, pp. 247–255, 1989.

Mazerolles et al., Cell, vol. 55, pp. 497–504, Nov. 1988.

Urban, J.L., et al., Autoimmune T Cells: "Immune Recognition of Normal and Variant Peptide Epitopes and Peptide–Based Therapy", *Cell*, 59:257–271 (1989).

Wraith, D.C., et al., "Antigen Recognition in Autoimmune encephalomyelitis and the Potential for Peptide–Mediated Immunotherapy", *Cell*, 59:247–255 (1989).

PCT/US90/00085 (WO 90/08161) 6 Jul. 1990.

*Primary Examiner*—Avis M. Davenport

*Attorney, Agent, or Firm*—Townsend and Townsend and Crew LLP

[57] ABSTRACT

Peptide compositions are provided which bind MHC molecules of interest and inhibit T cell activation. The peptide compositions of the present invention comprise various isosteres of naturally occurring amino acid sequences. Such compositions may be used to treat diseases associated with particular DR alleles, including autoimmune diseases such as rheumatoid arthritis.

17 Claims, 5 Drawing Sheets

Aryl, Arylalkyl and Styryl caps (Aryl=phenyl, 1-Naphthyl, 2-Naphthyl)
Mono-, di-, or Tri- substituted aromatic caps.

Phenyl

Arylalkyl

Styryl

2-Naphthylalkyl

2-Naphthyl

1-Naphthylalkyl

1-Naphthyl n = 1-7

R = H, OH, OMe, OEt, OPh, $NH_2$, $NMe_2$, Cl, Br, $CH_3$, SMe

R' = H, OH, OMe, OEt, OPh, $NH_2$, $NMe_2$, Cl, Br, $CH_3$, SMe

Cycloalkyl and Cycloalkylalkyl Caps (n = 1-7, m = 0-8)

Cycloalkyl

Cycloalkyalkyl

R = H, OH, OMe, OEt, OPh, $NH_2$, $NMe_2$, $CH_3$, SMe

R' = H, OH, OMe, OEt, OPh, $NH_2$, $NMe_2$, $CH_3$, SMe

R" = H, OH, OMe, OEt, OPh, $NH_2$, $NMe_2$, $CH_3$, SMe

Adamantyl and Adamantylalkyl Caps (n = 1-7)

1-Adamantyl

1-Adamantylalkyl

2-Adamantyl

2-Adamantylalkyl

Heteroaryl, Heteroarylalkyl Caps with 1, 2, or 3 Nitrogen Atoms

Mono-, di-, trisubstituted Pyridines

Mono-, di-, tri-substituted Pyrazines

Mono-, di-, tri-substituted Triazines n = 1-7

R = H, OH, OMe, OEt, OPh, $NH_2$, $NMe_2$, $CH_3$, SMe

R' = H, OH, OMe, OEt, OPh, $NH_2$, $NMe_2$, $CH_3$, SMe

Other Heterocyclic Caps

Mono-, di-, tri-substituted
Thiazoles
Oxazoles
Imidazoles

Mono-, di-, tri-substituted Isoxazoles n= 1-7

X = O, NH, S, $CH_2$

R = Me, Et, OMe, OEt, SMe, SEt

IMMUNOSUPPRESSANT PEPTIDES

This is a continuation of application Ser. No. 08/143,973, filed Oct. 27, 1993, which is a continuation of application Ser. No. 07/654,482, filed Feb. 12, 1991, both now abandoned.

BACKGROUND OF THE INVENTION

The present invention relates generally to the field of peptide therapy and, more particularly, to the use of novel peptides which bind to major histocompatibility complex (MHC) molecules and modulate an immune response.

An integral part of the mammalian immune response is the ability of T cells to recognize protein antigens. The T cells are presented with processed antigen complexed with the MHC molecules expressed on the surface of certain cells. Antigen presentation appears to be a major, if not the primary, function of MHC molecules.

Both helper and cytotoxic T cells are believed to recognize antigens by interacting with MHC-antigen complexes. MHC Class I molecules (e.g., HLA-A, -B and -C molecules in the human system) are involved in generating a T killer cell response, where cells bearing the eliciting antigen are attacked. Class II molecules (HLA-DP, -DQ and -DR in humans) present antigen to T-helper cells, and thus control the expansion and maturation of a selected population of B cells, resulting in the production of antigen-specific antibodies. Thus, Class I and Class II MHC molecules play a critical role in regulating an individual's immune response to a protein antigen.

Autoimmune diseases are characterized by an immune response against "self" antigens. In essence, autoimmune disease results when an individual's immune response is no longer able to distinguish self antigens from non-self (foreign) antigens. It is thought that self-reactive B cells exist in the body for many potential autoantigens. The reactivity of the self-reactive B cells and other immune cells is likely controlled, however, by MHC molecules.

Several autoimmune diseases have been associated with particular MHC alleles. One of the most notable associations has been a rheumatoid syndrome involving the spinal column, ankylosing spondylitis, and the allele HLA-B27. Another, the haplotype HLA-DR2, is common in the autoimmune disease multiple sclerosis. Hashimoto's disease, which affects the thyroid, tends to be associated with HLA-DR5. Other studies have shown that individuals having HLA-DR1, and/or DR4w4 and/or DR4w14 alleles are genetically predisposed towards rheumatoid arthritis. Research suggests that the corresponding MHC proteins play a key role in such diseases, perhaps by binding with a self-antigen and presenting it to T cells.

Current treatment for autoimmune disease consists primarily of treating the symptoms, but not intervening in the etiology of the disease. Broad spectrum chemotherapeutic agents are typically employed, which agents are often associated with numerous undesirable side effects. For instance, a variety of agents have been used to manage rheumatoid arthritis: i) non-steroidal anti-inflammatory drugs may alleviate pain, swelling, and tissue destruction in some patients, but are often associated with ulcers, kidney damage and gastrointestinal upset; ii) injectable gold salts may induce a remission of the disease, but are associated with lesions of the mucous membranes, kidney damage, and accelerated degradation of platelets; iii) anti-malarial drugs and anti-cancer agents (e.g., methotrexate) have been used but may be severely toxic; and, iv) corticosteroids have been used with varying degrees of success and, unfortunately, frequent side effects.

The inadequate treatments presently available for rheumatoid arthritis illustrate the urgent need for agents to treat autoimmune diseases that avoid nonspecific suppression of an individual's overall immune response yet not causing serious side effects. Such agents should also be economical to produce and possess favorable pharmacologic properties which result in, e.g., a relatively long half-life, thereby facilitating lower dosages and/or less frequent administration. The present invention fulfills these and other related needs.

SUMMARY OF THE INVENTION

The present invention provides compositions comprising peptides which inhibit HLA-DR restricted T cell activation by binding to HLA-DR molecules, such as DR1, DR4w4, or DR4w14.

The formula for the peptides is, in a direction from the N- to C- terminus:

$$R_1—R_2—R_3—R_4—R_5$$

In the above formula, $R_1$ is a spacer sequence of from 0 to about 7 amino acid or amino acid mimetic residues, $R_2$ is a hydrophobic L-amino acid or L-amino acid mimetic residue, $R_3$ is spacer sequence of from 2 to about 6 L-amino acid or L-amino acid mimetic residues, $R_4$ is T or a T mimetic residue, and $R_5$ is a spacer sequence of between 0 and about 10 amino acid or amino acid mimetic residues.

The peptide further contains one or more of the following modifications: if $R_1$ is present, the last residue of $R_1$ defines with $R_2$ an isostere of $X_1$-F; $R_3$ comprises 2–5 residues, two of which define an isostere of $X_2$-Q; or the last residue of $R_3$ defines with $R_4$ an isostere of $X_3$-T, wherein $X_1$ is a L- or D-amino acid mimetic and $X_2$ and $X_3$ can be any L-amino acid or L-amino acid mimetic.

In one embodiment, the last residue of $R_1$ ($X_1$) is neutral, positively or negatively charged. Preferably, it will be K, R, D, or E and the isostere of X-F will be K-F, R-F, K-Y, R-Y, A-F, aF, kF, fF, kY, rY, D-F, E-F, D-Y, EY, dF, eF, dY, or eY. The isostere of $X_{2}$-$_{Q}$ is preferably R-Q. The isosteres described above may comprise either a peptide bond or an amide bond mimic.

In another embodiment, the group $R_1$ contains 3 residues, with the first residue being a D-amino acid, preferably y, f, or a. The group may also comprise at least one N-alkyl or α-alkyl amino acid residue. $R_2$ is thought to be a critical binding site residue and is preferably F, Y, cyclohexylalanine, or adamantylalanine. $R_3$ usually comprises 4 residues, composed of QSQT, QRQT, ARAT, AAAT, AAAA, AAAR, AAAK or AKAA. $R_5$ is frequently 5 residues long, the last residue being a D-amino acid. Preferred sequences are AAAAa, KAAAa, LKLAt, LKAAa, and AKAAa.

The peptide has a core binding region composed of L-amino acids which determines binding affinity. The core binding region will typically include, in the direction from the N- to the C-terminus, a hydrophobic L-amino acid or L-amino acid mimetic, a spacer sequence of from about 2 to about 6 residues, and a T or T mimetic residue. Preferred sequences of the core binding region are F-Q-R-Q-T-T, F-A-A-A-A-T, or F-A-A-A-K-T.

Finally, a pharmaceutical composition comprising a suitable carrier and the peptides of the present invention is provided. Methods of treating autoimmune-associated disorders comprising administering an effective amount of the pharmaceutical composition are also provided. The disorder can be a rheumatoid disorder, such as rheumatoid arthritis.

The composition can be administered in a variety of ways, such as orally, intravenously, intramuscularly, subcutaneously, or by aerosol.

DESCRIPTION OF THE PREFERRED EMBODIMENTS

Figure 1:
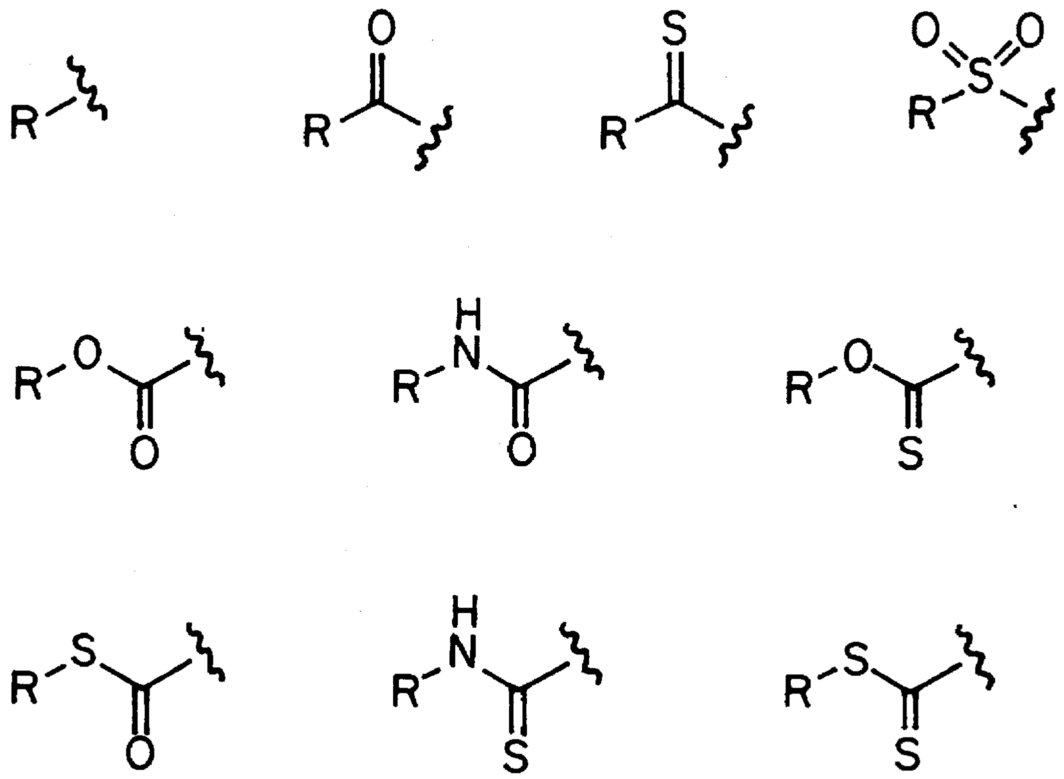
FIG. 1 shows suitable linkages for linking hydrophobic caps to the N-terminus of peptides of the present invention.

Compositions and methods are provided by the present invention for treating autoimmune-associated disorders. Autoimmune diseases are typified by an immune response against a host antigen, the consequences of which can be severe. The present invention provides the ability to intervene and block, or at least inhibit, antigen specific immune responses associated with predetermined MHC molecules.

The compositions of the invention comprise peptides which bind to an MHC molecule or molecules associated with a particular autoimmune-related disorder. The peptides may be derived from a sequence found in an antigen or hapten which binds to an MHC molecule associated with the disease or disorder of interest. Thus, the peptides of interest are typically identified from antigens commonly associated with a particular disease, or from a screening protocol.

A number of autoimmune-associated disorders have been associated with specific MHC molecules. For instance, in humans the disease rheumatoid arthritis has been associated with the HLA-DR alleles DR1, DR4w4 and DR4w14. Similarly, as mentioned above, ankylosing spondylitis has been closely associated with the presence of the a Class I allele, HLA-B27, myasthenia gravis has been associated with HLA-DR3 and -DR5, and multiple sclerosis has been associated with DR2.

By way of example and not limitation, as HLA-DR alleles have been associated with rheumatoid arthritis, antigens which bind to the DR molecule may serve as a source of peptide sequences for the present invention. Hemagglutinin ("HA") is a protein identified as specifically reacting with HLA -DR, and portions thereof are screened for reactivity to provide a sequence which binds the appropriate DR molecule, such as DR1, DR4w4 or DR4w14, and are then screened for the ability to inhibit or otherwise modulate an antigen-specific immune response such as might be associated with the disease. The MHC molecule with which the peptide is being tested may be isolated from cells which express it, or the cells may be used intact. A large number of cells with defined MHC molecules, particularly MHC Class II molecules, are known and readily available to the artisan. A variety of assay procedures may be employed in the screening protocol and are also well known in the art. Typically, for instance, the peptide may be labelled, e.g., with a radionuclide, enzyme, fluorescer, etc. and specific binding activity determined.

Using the procedure outlined herein, a sequence of HA, amino acid residues 307 to 319 (designated here as peptide I or HA307–319), has been identified which binds to both DR1 and DR4w4 MHC molecules. The sequence of this peptide is as follows:

Peptide I

```
307         310                         315                 319
Pro—Lys—Tyr—Val—Lys—Gln—Asn—Thr—Leu—Lys—Leu—Ala—Thr
```

It should be understood that the nomenclature used to describe peptide compounds follows the conventional practice wherein the amino group is presented to the left (the N-terminus) and the carboxy group to the right (the C-terminus) of each amino acid residue. In the formulae representing selected specific embodiments of the present invention, the amino- and carboxy-terminal groups, although not specifically shown, will be understood to be in the form they would assume at physiologic pH values, unless otherwise specified. In the amino acid structure formulae, each residue is generally represented by a three letter or single letter designation, in accordance with the following:

| Amino Acid | Three-Letter Symbols | One-Letter Symbols |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In the present application, the L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The biological activity of the peptide, e.g., that ability to inhibit antigen-specific T cell activation, may also be assayed in a variety of systems. In one exemplary protocol, an excess of peptide is incubated with an antigen-presenting cell of known MHC expression, (e.g., DR1) and a T cell clone of known antigen specificity (e.g., tetanus toxin 830–843) and MHC restriction (again, DR1), and the antigenic peptide itself (i.e., tetanus toxin 830–843). The assay culture is incubated for a sufficient time for T cell proliferation, such as four days, and proliferation is then measured using standard procedures, such as pulsing with tritiated thymidine during the last 18 hours of incubation. The percent inhibition, compared to the controls which received no inhibitor, is then calculated.

The capacity of peptides to inhibit antigen presentation in an in vitro assay has been correlated to the capacity of the peptide to inhibit an immune response in vivo. In vivo activity may be determined in animal models, for example, by administering an antigen known to be restricted to the particular MHC molecule recognized by the peptide, and the immunomodulatory peptide. T lymphocytes are subsequently removed from the animal and cultured with a dose range of antigen. Inhibition of stimulation is measured by conventional means, e.g., pulsing with [$^3$H]-thymidine, and comparing to appropriate controls. Certain experimental details will of course be apparent to the skilled artisan. See also, Adorini, et al., *Nature* 334:623–625 (1988), incorporated herein by reference.

Once an antigen or peptide thereof which binds to the selected MHC molecule is identified, a "core binding region" of the antigen or peptide may be determined by, e.g. synthesizing overlapping peptides, and/or employing N-terminal or C-terminal deletions (truncations) or additions. In the determination of a core binding region and critical contact residue, a series of peptides with single amino acid substitutions may be employed to determine the effect of electrostatic charge, hydrophobicity, etc. on binding. For instance, with peptide I, a series of positively charged (e.g., Lys or Arg) or negatively charged (e.g., Glu) amino acid substitutions were made along the length of the peptide revealing different patterns of sensitivity towards various DR molecules. For example, the DR4w4 molecule preferentially binds to peptides that bear little or no electrostatic charge in a core region. Notably, substitution of Tyr 309 of peptide I with either Glu or Arg results in substantially decreased binding affinity.

Within the core region, "critical contact sites," i.e., those residues (or their functional equivalents) which must be present in the peptide so as to retain the ability to bind an MHC molecule and inhibit the presentation to the T cell, may be identified by single amino acid substitutions, deletions, or insertions. In addition, one may also carry out a systematic scan with a specific amino acid (e.g., Ala) to probe the contributions made by the side chains of critical contact residues. For example, Ala substitutions along the length of HA peptide I reveals that binding to the DR1 molecule is relatively unaffected by such substitutions, except for an Ala substitution of position Tyr-309. Binding to DR4w4 is relatively unaffected by Ala substitutions, except at positions Tyr-309 and Thr-314.

Peptides of the invention which are relatively insensitive to single amino acid substitutions with neutral amino acids, except at essential contact sites, have been found to tolerate multiple substitutions. Particularly preferred multiple substitutions are small, relatively neutral moieties such as Ala, Gly, Pro, or similar residues. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule may also be achieved by such substitutions, compared to the affinity of the parent peptide. In any event, such "spacer" substitutions should employ amino acid residues or other molecular fragments chosen to avoid, for example, steric and charge interference which might disrupt binding.

The effect of single amino acid substitutions may also be probed using D-amino acids. Such substitutions may be made using well known peptide synthesis procedures, as described in e.g., Merrifield, *Science* 232:341–347 (1986), Barany and Merrifield, *The Peptides*, Gross and Meienhofer, eds. (N.Y., Academic Press), pp. 1–284 (1979); and Stewart and Young, *Solid Phase Peptide Synthesis*, (Rockford, Ill., Pierce), 2d Ed. (1984), incorporated by reference herein.

Single D-amino acid substitutions in HA peptide I reveal that those made to the core region produce a peptide having substantially decreased affinity for MHC DR1, whereas those D-form substitutions made outside a core region are relatively well tolerated. In peptides of the present invention, as well, D-amino acid substitutions in the core binding region ($R_2$ to $R_4$) substantially decrease affinity for MHC molecules. Thus, the core binding region of these peptides is comprised only of L- amino acids or L-amino acid mimetics.

A preferred embodiment of the peptides of the present invention comprises modifications to the N- and C-terminal residues. As will be well understood by the artisan, the N- and C-termini may be modified to alter physical or chemical properties of the peptide, such as, for example, to affect binding, stability, bioavailability, ease of linking, etc.

The N terminal residue can be modified to include hydrogen, or alkyl, cycloalkyl, aryl, arylalkyl, and acyl groups. The N-terminal residue may be linked to a variety of moieties other than amino acids such as polyethylene glycols (such as tetraethylene glycol carboxylic acid monomethyl ether), pyroglutamic acid, succinyl, methoxy succinyl, benzoyl, phenylacetyl, 2-, 3-, or 4-pyridylalkanoyl, aroyl, alkanoyl (including acetyl and cycloalkanoyl), arylalkanoyl (including pyridyls), arylaminocarbonyl, alkylaminocarbonyl, cycloalkylaminocarbonyl, alkyloxycarbonyl (carbamate caps), cycloalkoxycarbonyl, among others.

Preferred modifications of the C-terminus include modification of the carbonyl carbon of the C-terminal residue to form a carboxy-terminal amide or alcohol (i.e., as reduced form). In general, the amide nitrogen, covalently bound to the carbonyl carbon on the C-terminal residue, will have two substitution groups, each of which can be hydrogen, alkyl or an alkylaryl group (substituted or unsubstituted). Preferably the C-terminal is an amido group, such as $-CONH_2$, $-CONHCH_3$, $-CONHCH_2C_6H_5$ or $-CON(CH_3)_2$, but may also be 2-, 3-, or 4-pyridylmethyl, and 2-, 3-, or 4-pyridylethyl, carboxylic acid, ethers, carbonyl esters, alkyl, arylalkyl, aryl, cyclohexylamide, piperidineamide and other mono or disubstituted amides. Other moieties that can be linked to the C-terminal residue include piperidine-4-carboxylic acid and cis- or trans-4-aminocyclohexanecarboxylic acid.

In forming C-terminal amidated compounds of the present invention, the compound can be synthesized directly, for example, using an amine and an oxime resin, Kaiser et al., *Science* 243:187 (1989), incorporated herein by reference, or using a methyl benzhydryl amine (MBHA) polystyrene resin. Alternatively, the amidated compounds may be chemically amidated subsequent to peptide synthesis using means well known to the art, or enzymatically amidated. C-terminal alcohols and corresponding ethers can be prepared by methods well known to those skilled in the art. Fully protected peptides suitable for C-terminal amidation are conveniently prepared by solid phase synthesis using the SASRIN resin in conjunction with an FMOC synthesis protocol. See, e.g., Mergler et al., *Tet. Letters* 29:4005–4008 (1988), which is incorporated herein by reference.

Modifications of peptides with various amino acid mimetics or D-amino acids, for instance at the N- or C-termini, are useful in increasing the stability of the peptide in vivo. The peptides of the present invention preferably have a human serum half life at least about two times that of peptide I, preferably about four to ten times greater. Peptides with half lives greater than ten times that of peptide I are particularly preferred. Stability can be assayed in a number of ways. For instance, peptidases and various biological media, such as human plasma and serum, have been used to test stability. See, e.g., Verhoef et al., *Eur. J. Drug Metab. Pharmacokin.* 11:291–302 (1986); Walter et al., *Proc. Soc. Exp. Biol. Med.* 148:98–103 (1975); Witter et al., *Neuroendocrinology* 30:377–381 (1980); Verhoef et al., *J. Endocrinology* 110:557-562 (1986); Handa et al., *Eur. J. Pharmacol.* 70:531–540 (1981); Bizzozero et al., *Eur. J. Biochem.* 122:251–258 (1982); Chang, *Eur. J. Biochem.* 151:217–224 (1985), all of which are incorporated herein by reference. A preferred method for determining stability is to measure half life in the 25% human serum assay described in detail below.

$R_1$, $R_3$, and $R_5$, as previously described, are spacer sequences. They comprise neutral and positively charged residues. The neutral residues of the spacer sequences typically include, among others, Ala, ala, Gly, Pro, β-Ala, substituted β-ala (e.g. α-methyl, β-methyl, α-benzyl, or β-benzyl substituted), PABA, or other neutral spacers of nonpolar amino acids (those with hydrophobic side groups at physiologic pH values), such as aminoisobutyric acid (Aib), Val, Leu, Ile, Met, Phe, or Trp; or other neutral polar amino acid (those residues with hydrophilic, uncharged side groups at physiologic pH), such as Ser, Thr, Asn, Gln. A spacer sequence may also include amino acid mimetics such as ethylene glycol or propylene glycol.

Positively charged residues are incorporated in the spacer sequences to increase aqueous solubility. The presence of these residues generally increases solubility to at least about 1 μg/ml and in some cases, higher than 1 mg/ml at pH 7.4. Positively charged spacer residues include, among others, Lys, homo-Lys, Arg, N- or N-dialkyl-Lys, homo-Arg, N-,N-dialkyl-homo-Arg, N-or N,N-dialkyl-Arg, N,N,N-trialkylammonium salts, ornithine (Orn), 2, 3-diaminopropanoic acid (dap), 2,4-diaminobutanoic acid (dab), and may have, for example, molecules such as dimers of ethylene glycol (polyethylene glycol or propylene glycol (polypropylene glycol) attached thereto, e.g., to Lys, to further enhance solubility.

$R_3$ is a spacer sequence within the core binding region. As discussed above, the core binding region ($R_2$ to $R_4$) of a peptide of the present invention does not contain D-amino acids. Thus, the above description of the residues in $R_1$ and $R_5$ applies to $R_3$ except that all the $R_3$ amino acid residues are in the L-form.

$R_2$, as previously described, is a hydrophobic residue and is thought to be a binding site contact residue. Although its selection is generally dependent on the particular MHC molecule of interest, the $R_2$ residue may generally be selected from, among others, the group of Tyr, Phe, Trp, Met, and their amino acid mimetics, such as, β-2-thienylalanine, -α-amino-4-phenylbutyric acid, phenylglycine, 3-(2-naphthyl) alanine, 3-(1-naphthyl) alanine, β-1-adamantyl-alanine, β-9-anthracenylalanine, 3-cylohexylalanine, 2-amino-3(1,1'-biphenyl-4-yl)-propanoic acid, 2-aminoindane-2-carboxylic acid, tetrahydroisoquinoline carboxylic acid, 1-(2-propanoic acid)-3-amino-benzazepine-2-one, and 3-(4-pyridyl)-alanine. In certain preferred embodiments, $R_2$ is Phe or Tyr, particularly when the MHC molecule is DR1, DR4w4, and DR4w14, but other hydrophobic amino acid mimetics may also be substituted.

In addition, if $R_1$ is absent, $R_2$ may be any of a number of non-amino acid hydrophobic moieties which form a hydrophobic "cap" at the N-terminus. These moieties are preferably amino acid mimetics which do not interfere with recognition of the peptide by the MHC molecule and increase serum half life by increasing peptidase resistance of the peptide.

The N-terminal hydrophobic moiety can be linked to the amino terminus (e.g., an $R_1$ residue; $R_2$, if $R_1$ is absent; or $R_3$, if the hydrophobic moiety is $R_2$) through any of a number of linkages such as peptide backbone modifications known to those skilled in the art (see, Spatola, *Chemistry and Biochemistry of Amino Acids, Peptides and Proteins*, Vol. VII (Weinstein ed., 1983), which is incorporated herein by reference). Linkages suitable in the present invention include those illustrated in FIG. 1.

Figure 2:
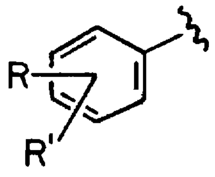
FIG. 2 shows various aryl, alkyl, styryl, and substituted aromatic N-terminal caps for peptides of the present invention.
Figure 2:
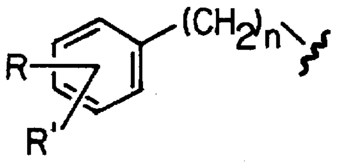
Figure 2:
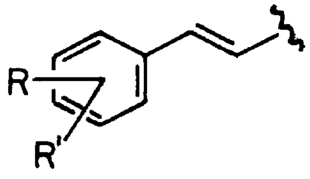
Figure 2:
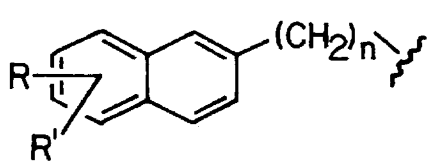
Figure 2:
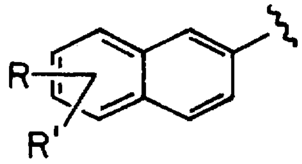
Figure 2:
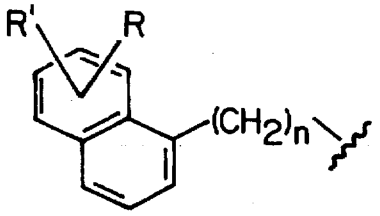
Figure 2:
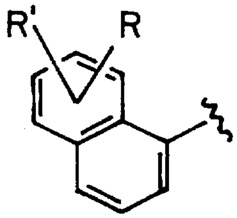
Figure 3:
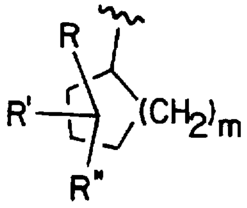
FIG. 3 shows various cycloalkyl and cycloalkylalkyl N-terminal caps for peptides of the present invention.
Figure 3:
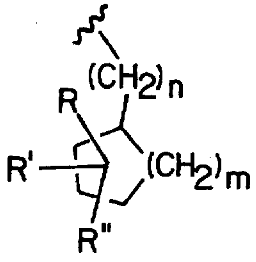
Figure 4:
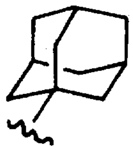
FIG. 4 shows various adamantyl and adamantyl alkyl N-terminal caps for peptides of the present invention.
Figure 4:
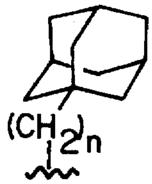
Figure 4:
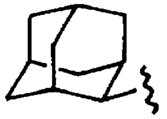
Figure 4:
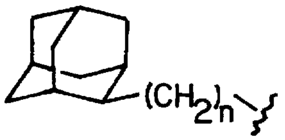
Figure 5:
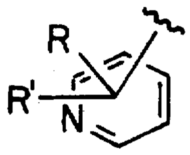
FIG. 5 shows various heteroaryl and heteroarylalkyl N-terminal caps for peptides of the present invention.
Figure 5:
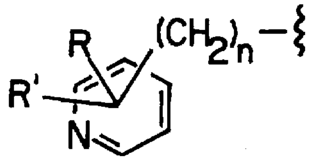
Figure 5:
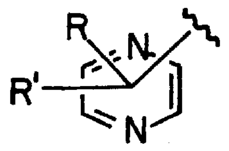
Figure 5:
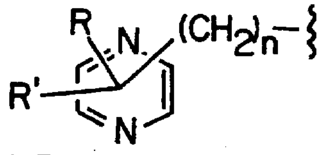
Figure 5:
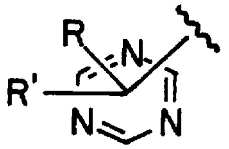
Figure 5:
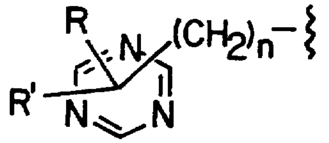
Figure 6:
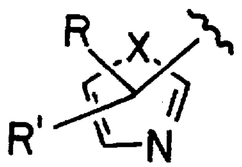
FIG. 6 shows various heterocyclic N-terminal caps for peptides of the present invention.
Figure 6:
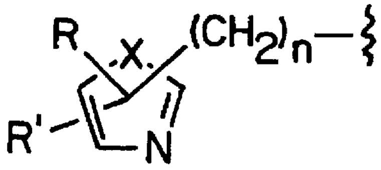
Figure 6:
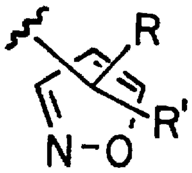
Figure 6:
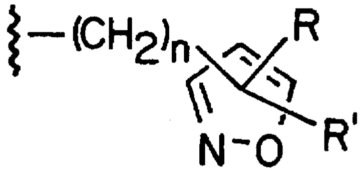

A wide variety of N-terminal caps (e.g., amino acid mimetics) can be used so long as MHC binding is not affected and serum half life is improved. Examples of suitable N-terminal moieties include aryl (including phenyl, 1-Naphthyl, and 2-Naphthyl), arylalkyl, styryl, and mono-, di-, and tri-, substituted moieties (FIG. 2); cycloalkyl and cycloalkylalkyl moieties (FIG. 3); adamantyl and adamantylalkyl moieties (FIG. 4); heteroaryl, heteroalkyl, and other heterocyclic moieties with 1, 2 or 3 nitrogen atoms (FIGS. 5 and 6).

$R_4$, as previously defined is thought to be binding site contact residue. It is preferably a T, or a T mimetic, such as H, G, V, P, S, alkyl substituted His, hydroxyproline, hydroxyvaline, 3-acetyl-2,3-diaminoproanoic,4-acetyl-2,4-diaminobutanoic acid, allothreonine, and the like.

Peptides of the present invention possess various combinations of the above features. For instance, virtually any residue of peptide I may be substituted with one of the D-amino acids or amino acid mimetics discussed above. Alternatively, one or both terminal residues may be modified as described above. In certain embodiments both terminal residues are modified D-amino acids, for instance, the C-terminal residue is amidated and the N-terminal residue is acetylated. In addition, the C-terminal residue can be an isostere of the dipeptide A—A (such as piperidine-4-carboxylic acid or cis-4-aminocyclohexanecarboxylic acid) and the N-terminal residue can be a D-amino acid. In other embodiments $R_1$ may be absent and $R_2$ is a hydrophobic amino acid mimetic which forms a hydrophobic cap. Any combination of the modifications and substitutions discussed can be used so long as MHC binding is not adversely affected.

Peptides or analogs thereof having the desired activity may be modified as necessary to provide certain desired attributes, e.g., improved pharmacological characteristics, while increasing or at least retaining substantially all of the biological activity of the unmodified peptide to inhibit the preselected immune response. For instance, the peptides can be modified by extending, decreasing or substituting in the compound's amino acid sequence, e.g., by the addition or deletion of amino acids on either the amino terminal or carboxy terminal end, or both, of the sequences disclosed above.

The peptides or analogs of the invention can be modified by altering the order or composition of certain residues, it being readily appreciated that certain amino acid residues essential for biological activity, e.g., those at critical contact sites, may generally not be altered without an adverse effect on biological activity. The non-critical amino acids need not be limited to those naturally occurring in proteins, such as L-α-amino acids, or their D-isomers, but may include non-protein amino acids as well, such as β-γ-δ-amino acids, as well as many derivatives of L-α-amino acids. As discussed, a peptide of the present invention may generally comprise either L-amino acids or D-amino acids, but not D-amino acids within a core binding region.

The peptides and analogs thereof of the present invention which bind to MHC molecules and inhibit or block MHC restricted antigen-specific T cell activation will generally comprise at least 4 amino acid residues or the conformational equivalent thereof, more usually at least 6, more often at least about 8 and frequently at least about 13 residues long, and usually will not exceed up to about 28 residues or the equivalent thereof in length, more typically 14 residues or less, and preferably no more than about 18 to 25 amino acid residues or the equivalent thereof in length. As mentioned above, it is understood that non-critical amino acids may be substituted with other amino acids or with amino acid mimetics; in instances where spacer molecules are substituted for non-essential residues, the approximate length of the resulting peptide should generally not exceed that which may be accommodated by the binding domain of the selected MHC molecule.

The peptides of the present invention and pharmaceutical compositions thereof are particularly useful for administration to vertebrates, particularly humans and other mammals, to treat a variety of conditions involving autoimmune diseases. For instance, although rheumatoid arthritis can be treated with conventional chemotherapeutic agents as mentioned above, the peptides of the invention as described herein may be used to treat the symptoms of rheumatoid arthritis or prevent their occurrence in identified patients or those patients at risk of developing the disease. Since the immunomodulatory peptides which bind to selected MHC molecules are more selective than conventional agents, and generally will be less toxic, they will be more effective and less likely to cause complications than the conventional broad spectrum agents. Of course, if necessary or desirable, the peptides may be administered in conjunction with the traditional chemotherapeutic agents, and may be used to lower the dose of such agents to levels substantially below those typically associated with toxicity.

Other autoimmune associated disorders for which the peptides of the invention may be employed to relieve the symptoms of, treat or prevent the occurrence or reoccurrence of include, for example, Sjogren syndrome, scleroderma, polymyositis, dermatomyositis, systemic lupus erythematosus, juvenile rheumatoid arthritis, ankylosing spondylitis, myasthenia gravis (antibodies to acetylcholine receptors), bullous pemphigoid (antibodies to basement membrane at dermal-epidermal junction), pemphigus (antibodies to mucopolysaccharide protein complex or intracellular cement substance), glomerulonephritis (antibodies to glomerular basement membrane), Goodpasture's syndrome, autoimmune hemolytic anemia (antibodies to erythrocytes), Hashimoto's disease (antibodies to thyroid), pernicious anemia (antibodies to intrinsic factor), idiopathic thrombocytopenic purpura (antibodies to platelets), Grave's disease, and Addison's disease (antibodies to thyroglobulin), and the like.

The dose of the immunomodulatory peptides of the invention for treatment of autoimmune disease will vary according to, e.g., the peptide composition, the manner of administration, the particular disease being treated and its severity, the overall health and condition of the patient, and the judgment of the prescribing physician. For example, for the treatment of rheumatoid arthritis with a peptide of the present invention the dose is in the range of about 50 μg to 2,000 mg/day, preferably 5 to 700 mg/day for a 70 kg patient. Administration should begin at the first sign of symptoms or shortly after diagnosis, and continue at least until symptoms are substantially abated and for a period thereafter. In established cases loading doses followed by maintenance doses may be required.

The pharmaceutical compositions are intended for parenteral, topical, oral or local administration, such as by aerosol or transdermally, for prophylactic and/or therapeutic treatment. The compositions are suitable for use in a variety of drug delivery systems. For a brief review of present methods for drug delivery, see, Langer, *Science* 249:1527–1533 (1990), which is incorporated herein by reference. Preferably, the pharmaceutical compositions are administered parenterally, i.e., intraarticularly, intravenously, subcutaneously, or intramuscularly. Thus, this invention provides compositions for parenteral administration which comprise a solution of the immunomodulatory peptide molecules dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of immunomodulatory peptides, which may be combined to form a peptide "cocktail" under certain circumstances for increased efficacy, in the pharmaceutical formulations can vary widely, i.e., from less than about 0.01%, usually at or at least about 5% to as much as 50 to 75% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 10 mg of peptide. Actual methods for preparing parenterally administrable compounds will be known or apparent to those skilled in the art and are described in more detail in for example, *Remington's Pharmaceutical Sciences,* 17th ed., Mack Publishing Company, Easton, Pa. (1985), which is incorporated herein by reference.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, preferably 25%–75%.

For aerosol administration, the immunomodulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided peptide(s) and surfactant. The ingredients are thus maintained at an elevated pressure until released by action of the valve.

The compositions containing the immunomodulatory peptides can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient, but generally range from about 0.1 mg to about 2,000 mg of peptide per day for a 70 kg patient, with dosages of from about 0.5 mg to about 1,000 mg of peptide per day being more commonly used. It must be kept in mind that the materials of the present invention may generally be employed in serious disease states, that is, life-threatening or potentially life threatening situations. In such cases, in view of the minimization of extraneous substances, the relative nontoxic nature and the general lack of immunogeneticity of peptides, it is possible and may be felt desireable by the treating physician to administer substantial excesses of these immunomodulatory compositions.

In prophylactic applications, compositions containing the peptides of the invention are administered to a patient susceptible to or otherwise at risk of a particular autoimmune disease to enhance the patient's own immunoregulatory capabilities. Such an amount is defined to be a "prophylactically effective dose." In this use, the precise amounts again depend on the patient's state of health and weight, but generally range from about 0.1 mg to about 500 mg per 70 kilogram patient, more commonly from about 0.5 mg to about 200 mg per 70 kg of body weight.

Single or multiple administrations of the compositions can be carried out with dose levels and pattern being selected by the treating physician. In any event, the pharmaceutical formulations should provide a quantity of immunomodulatory peptide of this invention sufficient to effectively treat the patient.

The peptides may also find use as diagnostic reagents. For example, a peptide may be used to determine the susceptibility of a particular individual to a treatment regimen which employs the peptide or related peptides, and thus may be helpful in modifying an existing treatment protocol or in determining a prognosis for an affected individual. In such instances cells bearing the selected MHC antigen, e.g., white blood cells, will be obtained from the individual, incubated in vivo with the peptide(s), an immunostimulatory peptide, and a collection of T cells from the same individual. The proliferation of the T cells can then be assayed in the presence or absence of said immunomodulatory peptide or peptide mixture.

Definitions

"Alkyl" as used herein means a branched or unbranched saturated hydrocarbon chain containing 1–8 carbon atoms, including lower alkyls of 1–7 carbons such as methyl, ethyl, n-propyl, butyl, n-hexyl, and the like, cycloalkyls (3–7 carbons), cycloalkylmethyls (4–8 carbons), and arylalkyls.

The term "aryl" refers to a radical derived from an aromatic hydrocarbon by the removal of one atom, e.g., phenyl from benzene. The aromatic hydrocarbon may have more than one unsaturated carbon ring, e.g., naphthyl.

The term "spacer sequence" refers to sequences of amino acids or amino acid mimetics, which are substantially uncharged or positively charged under physiological conditions and which may have linear or branched side chains.

By "mimetics" as used herein is meant a moiety, other than a naturally ocurring amino acid, that conformationally and functionally serves as a substitute for a particular amino acid in a peptide of the present invention without adversely interfering to a significant extent with, or in some circumstances actually enhancing, the interaction of the peptide with its MHC receptor. Peptides incorporating amino acid mimetics may be synthesized and screened for effect on binding in a variety of assays, e.g., in a competition assay with an unsubstituted parent peptide. For a general discussion of peptide mimetics, see, Morgan and Gainor, *Ann. Repts. Med. Chem.* 24:243–252 (1989), which is incorporated by reference herein.

The term "residue" refers to an amino acid or amino acid mimetic incorporated in a polypeptide by an amide bond or amide bond mimetic.

By "core binding region" as used herein is meant a sequence of amino acids or amino acid mimetics important in maintaining a binding affinity of the peptide for an MHC molecule. The core binding region may contain contact residues having characteristics essential for binding. Thus, the core binding region comprises those residues of the peptide that define the specificity of the peptide-MHC interaction. See also, Sette et al., *Nature* 328:395–399 (1987), which is incorporated herein by reference, for a discussion of core binding regions.

The term "isostere" as used herein refers to a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, supra. Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH{=}CH]$. The nomenclature used above, follows that suggested by Spatola, supra. In this context, ψ indicates the absence of an amide bond. The structure that replaces the amide group is specified within the brackets.

Other possible modifications include, an N-alkyl (or aryl) substitution ($\psi[CONR]$), backbone crosslinking to construct lactams and other cyclic structures, or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr. Compared to the parent peptide, a retro-inverso peptide has a reversed backbone while retaining substantially the original spatial conformation of the side chains, resulting in a retro-inverso isomer with a topology that closely resembles the parent peptide and is able to bind the selected MHC molecule.

Various amino acid mimetics (as defined above) may be incorporated in the isostere. The side chain of the individual residues may also be modified in a number of ways. For instance, the side chain of a lysine residue isostere may be lengthened or shortened. Other modifications include, alkylation of $NH_2$ of lysine with a dihydroxypropyl radical.

The following examples are offered by way of illustration, not by way of limitation.

EXPERIMENTAL

EXAMPLE I

Selection and Screening of Peptide Library

This Example illustrates the method used to identify peptides which bound human MHC HLA-DR1 and -DR4w4. A library of about one hundred eighty synthetic peptides was tested. The library screened is nonredundant in the sense that care was taken to eliminate amino acid sequences too closely related; overlapping peptides were allowed but only if they overlapped less than 50% of total residues.

Cells. EBV-transformed homozygous cell lines were used as a source of DR molecules. Cell lines were routinely monitored for DR expression by FACS analysis. Their DR types were confirmed by serological typing (for example, see Terasaki et al., *Amer. J. Clin. Path.* 69:103–120 (1978)) and RFLP analysis (e.g., Schreuder, *J. Expt. Med.* 164:938 (1986)). Cell lines used were maintained in vitro by culture in RPMI 1640 medium (Flow Labs, McLeon, Va.), supplemented with 2 mM L-glutamine (Gibco, Grand Island, N.Y.), 50 mM 2-mercaptoethanol (Sigma Chemical Co., St. Louis, Mo.), 100 μg/ml streptomycin, 100 U/ml penicillin (Gibco, Grand Island, N.Y.), and 10% heat-inactivated fetal calf serum (Hazelton Biologics Inc., Lenexa, Kans.) or horse serum (Hazelton Biologics Inc.). Large quantities of cells were grown in stationary cultures (250 cc flasks). Cells were lysed at a concentration of $10^8$ cells/ml in 50 mM Tris-HCl pH 8.5, containing 2% Rennex, 150 mM NaCl, 5 mM EDTA, and 2 mM PMSF. The lysates were cleared of nuclei and debris by centrifugation at 10,000 ×g for 20 minutes.

Affinity purification of DR molecules. DR molecules were purified essentially as described by Gorga et al. (Gorga et al., *J. Biol. Chem.* 262:16087–16094 (1987)) using the monoclonal antibody LB3.1 (Gorga et al., *Cell. Immunol.* 103:160–173 (1986)), covalently coupled to protein A-Sepharose CL-4B. Epstein-Barr virus-transformed human B cell lines, homozygous at the DR locus, were used as a source of DR molecules. The LG-2 (DR1) and Preiss (DR4, Dw4) lines were obtained from Dr. J. C. Gorga (Harvard University, Cambridge, Mass.), and MAT (DR3), Beh (DR4, Dw4), and SWEIG (DR5) from Dr. G. Nepom (Virginia Mason Research Center, Seattle, Wash.). Aliquots Of cell lysates equivalent to approximately 10 g of cells were passed sequentially through the following columns: Sepharose CL-4B (10 ml), protein-A-Sepharose (5 ml), W6/32-protein-A-Sepharose (10 ml), LB3.1-protein A-Sepharose (15 ml), using a flow rate of 30 ml/h. The columns were washed with 10 column volumes of 10 mM Tris-HCl pH 8.0, 0.1% Rennex (5 ml/hr); 2 colE volumes of PBS and 1% octylglucoside. The DR was eluted with 0.05 M diethylamine in 0.15 M NaCl containing 1% octylglucoside (pH 11.5), immediately neutralized with 2M glycine pH 2.0 and concentrated by ultrafiltration through an Amicon YM-30 membrane. Protein content was evaluated by a BCA protein assay (Pierce) and confirmed by SDS PAGE electrophoresis.

Peptide synthesis. Peptides were synthesized on an Applied Biosystems (Foster City, Calif.) 430A peptide synthesizer according to well known protocols and radiolabeled when desirable as previously described. See, e.g., Merrifield, *Science* 232:341–347 (1986). The peptides were then purified by reversed-phase high-performance liquid chromatography (HPLC). The purity of the peptides was substantiated by amino acid sequence and/or composition analysis. They were routinely >95% pure after HPLC.

DR-peptide binding assay. Purified DR molecules (10–1,000 nM) were incubated with 10 nM $^{125}$I-radiolabeled peptide for 48 hours in the presence of added protease inhibitors. HPLC-purified peptides were radioiodinated ($^{125}$I) using the Chloramine T method, as previously described, (Buus et al., *Science* 235:1353–1358 (1987)). The final concentrations of protease inhibitors were: 1 mM PMSF, 1.3 mM 1,10-phenanthroline, 73 μM pepstatin A, 8 mM EDTA, 6 mM N-ethyl maleimide, and 200 μM Nα-p-tosyl-L-lysine chloromethyl ketone (TLCK). The final detergent concentration in the incubation mixture was 0.05% NP-40. Several of the peptides screened were hydrophobic and required DMSO to maintain solubility and reduce peptide adsorption to surfaces. In these instances peptide stock solutions were prepared in neat DMSO, and the final DMSO concentration in the incubation mixture was adjusted to 5%. Control experiments demonstrated that the ID 50% values obtained with or without DMSO were similar. The DR-peptide complexes were separated from free peptide by gel filtration on a Sephadex G50 (Pharmacia Fine Chemicals, Piscataway, N.J.) column (23×1.3 cm), as previously described. Id. The columns were eluted using PBS (0.5% NP-40, 0.1% $NAN_3$) collected in 1 ml fractions, which were then assayed for radioactivity. The fraction of peptide bound to DR (α) relative to the total amount of offered peptide was determined as the ratio of peptide in the void volume to the total peptide recovered. The α was corrected by subtracting the negative control ($^{125}$I-peptide incubated for two days at room temperature in the presence of protease inhibitors and 120 μg/ml of unlabeled peptide, but in the absence of any DR). Competitive inhibition by unlabeled peptide was used to determine ID 50% values. Id.

The results of the screening method with respect to DR1 are shown in Table 1 below, and the screening results for DR4w4 are shown in Table 2.

To obtain a figure that positively correlated with the binding affinity, the data were expressed as relative binding values. These can be roughly converted to micromolar concentrations by comparison with the parent peptide of the series as shown in the tables which follow. For each DR assay, peptides showing poor binding were not investigated further, whereas the better binders were retested and their activity quantified.

Binding capacities of the peptide libraries were sorted according to DR specificity, and the peptides, listed in descending order, are shown in Tables 1 and 2. Up to about twenty good binders have been identified for DR1, and approximately 6–8 peptides were identified which bound strongly to DR4.

TABLE 1

Representative L-Form Peptides Which Bind DR1

| Source | | Sequence | Relative Binding Affinity‡ |
|---|---|---|---|
| PT | 151–161 | RILAGALATYO | ++ |
| | | YTLLQAAPALDKLKLTGDEATGANI | ++ |
| NASE | 101–120 | EALVRQGHLAKVAYVYKPNNT | ++ |
| PT | 214–228 | SRRSVASIVGTLVRM | ++ |
| HA | 307–319 | PKYVKQNTLKLAT | +* |
| lambda rep | 14–18 3x | ARRLKARRLKARRLK | + |
| MAT | 19–31 | PLKAEIAQRLEDV | ± |
| P-CYTC | 88–104 | KAERADLIAYLKQATAK | ± |
| NASE | 1–20 | ATSTKKLHKEPATLIKAIDG | ± |
| | | YEHRVKRGLTVAVAGA | ± |
| OVA | 15–29 | DVRKELKVHHANENI | ± |
| TET TOX | 830–843 | QYIKANSKFIGITE | ± |
| CS | 382–398 | KIAKMEKASSVFNVVNS | ± |
| MYE BA . . . | 75–98 | GRTQDENPVVHFFKNIVTPRTPPP | ± |
| α2-μglobulin | 61–76 | SFYILAHTEFTPTETD | – |
| HEL | 1–18 | KVFGRCELAAAMKRHGLD | – |
| NASE | 21–40 | DTVKLMKGQPMTRFLLLVD | – |

‡Binding affinity relative to HA = 1, where affinity greater than 1.0 is "++", .51 to 1.0 is "+", 0.1 to .50 is "±", and less than 0.1 is "–".
*$K_D$ is approximately 5.6 nM.

TABLE 2

Representative L-Form Peptides Which Bind DR4w4

| Source | | Sequence | Relative Binding Affinity‡ |
|---|---|---|---|
| HA | 307–319 | PKYVKONTLKLAT | +* |
| Lol p I | Y224–240 | YEDVIPEGWKADTSYSAK | + |
| MYE BA . . . | 75–98 | GRTQDENPVVHFFKNIVTPRTPPP | ± |
| OVA | 15–29 | DVFKELKVHHANENI | – |
| β2-μglobulin | 61–76 | SFYILAHTEFTPTETD | – |
| NASE | 111–130 | VAYVYKPNNTHEQHLRKSEA | – |

‡Binding affinity relative to HA = 1, where affinity greater than 1.0 is "++", .51 to 1.0 is "+", 0.1 to .50 is "±", and less than 0.1 is "–".
*$K_D$ is approximately 5.6 nM.

EXAMPLE II

Peptide HA 307–319, ("Peptide I") having good binding activity for both DR1 and DR4w4 molecules, was chosen from the screening assays for further study. To determine the critical amino acids of Peptide I, the DR1, DR2, DR4w4 and DR4w14 binding capacities of a series of peptide I analogs with single or multiple amino acid substitutions were determined. To do this, peptides were tested for their ability to block an antigen-specific, HLA-D restricted T cell proliferative response. The protocol was as follows:

An EBV positive, DRi+homozygous typing cell line, LG-2, is washed 3× with Hank's Balanced Salt Solution (HBSS), suspended to $5\times10^6$/ml in HBSS, and fixed with 0.5% p-formaldehyde (w/v) at room temperature for 20 minutes. The fixed LG-2 cells are washed 1× with HBSS, washed 2× with RPMI media supplemented with L-glutamine, non-essential amino acids, sodium pyruvate, antibiotics, and 10% human sera type AB (Complete Media), resuspended at $10^6$/ml in Complete Media, and then plated as 100 μl into individual wells of a 96 well microtiter dish. The fixed LG-2 cells are then pulsed simultaneously for 2 hours at 37° C. with 50 μl of test peptide and 50 μl of stimulatory peptide which have been dissolved in Complete Media. The amount of stimulatory peptide added to each test well is constant and is calculated so as to yield 60–80% of the maximal T cell proliferative response. The potential inhibitor peptide is evaluated in duplicate at several concentrations corresponding to multiples of the stimulatory peptide concentration, usually 3×, 10×, 50×, and 250×. At the end of the two hour incubation the plates are centrifuged, and the media carefully aspirated and replaced with fresh media. The plates are washed in this manner three times in order to ensure complete removal of unbound peptide. At the end of the washes 50 μl of Complete Media remains in the well. In separate wells, increasing concentrations of stimulatory peptide are assayed in the absence of inhibitory peptide in order to obtain dose-response curves for the stimulatory peptide and to ensure that the amount of stimulatory peptide used in test wells is truly limiting.

Antigen-specific T cells are washed 2× in Complete Media, suspended to $2\times10^5$/ml in Complete Media, and plated as 150 μl into the wells containing the peptide-pulsed LG-2 cells. The cultures are incubated for three days at 37° C., and pulsed with 0.1 μCi/well of $^3$H-thymidine during the last 16 hours of culture. At the termination of the cultures the cells are harvested onto glass fiber and the amount of $^3$H-thymidine, which has been incorporated by the responder T cell, determined using liquid scintillation counting.

The results presented in Table 3 are expressed as the geometric mean of duplicate cultures. Binding affinity for each peptide is determined relative to either peptide I (HA 307–319) or a peptide having the sequence YARFQSQTTLKQKT. For each test peptide the amount of inhibition is plotted as a function of the ratio of inhibitor peptide/stimulator peptide, and this graph is used to determine a ratio of inhibitor peptide to stimulator peptide which yields 50% inhibition. These data are presented in the last two columns of Table 3. This 50% inhibitory value constitutes an additional means by which the MHC binding peptides can be compared.

Stability Assays

To analyze stability of the peptides, half life of the peptides was determined using a 25% human serum (v/v) assay. Using the procedure described below, the 25% human serum half life of peptide I was determined to be about 100 minutes. The protocol was as follows. Pooled human serum (Type AB, non-heat inactivated) was obtained from Irvine Scientific and was delipidated by centrifugation before use. Human serum was diluted to 25% with RPMI tissue culture media. All chemicals (reagent or HPLC grade) were purchased commercially from Sigma or Aldrich and used without further purification.

Typically, 1 mL of reaction solution in a 1.5 mL Eppendorf tube was temperature-equilibrated at 37°±° C. for 15 minutes before adding 5 μL of peptide stock solution (10 mg/mL in DMSO) to make the final peptide concentration 50 μg/mL. The initial time was recorded. At known time intervals 100 μL of reaction solution was removed and added to 200 μL of either 6% aqueous trichloracetic acid or ethanol. The cloudy reaction sample was cooled (4° C.) for 15 minutes and then spun at 14,000 rpm (Eppendorf centrifuge) for 2 minutes to pellet the precipitated serum proteins.

The following controls were carried out for each run: i) each set of stability experiments included a degradation study on a reference study on a reference peptide (Peptide I), carried out in separate solution, ii) peptide stability was also determined in precipitation supernatant containing 4% (or greater) trichloracetic acid to ensure that the peptides did not undergo acid-catalyzed degradation while awaiting HPLC sample analysis, iii) sample recovery upon TCA or ethanol precipitation of serum proteins was determined by comparison of the peptide peak area at time=0 with a peptide stock solution of known concentration in $DMSO/H_2O$ (1:1). Generally, 6% TCA showed the highest peptide recovery, but where less than 90% recovery in TCA was observed, EtOH was used; all peptides showed 85% or greater recovery in their optimal precipitation media and iv) peptide degradation was carried out under conditions where the degradation rate constant was independent of peptide concentration (demonstrated, for example, by lowering the peptide concentration or using radiolabeled peptide only), and proportionately dependent on biological media concentration.

Peptide analysis was carried out by reversed-phase HPLC using stability-specific chromatography conditions. Most samples were analyzed using a 5 μm 25×0.4 cm Vydac C-18 column and a 0→50% gradient (0.08% trifluoroacetic acid in water →0.08% trifluoroacetic acid in $CH_3CN$) over 40 minutes (flow=1 mL/minute, detection=214 nm, AUFS=0.2) at room temperature. Where peptide coeluted with a media peak or one of the peptide degradation product peaks, a different brand of C-18 column (for example, Waters Bondapak) was used to effect separation. HPLC linearity was determined for a representative group of peptides up to 50 μg/mL (three-fold higher than the concentration actually assayed for in the biological media samples) in $DMSO/H_2O$ (1:1). This mixed solvent system was chosen to minimize peptide loss due to adhesion to the reaction vessel. HPLC stability-specificity was carried out by traditional methods including: separate analysis of non-precipitated media peaks, analysis of peptide peak shape and peak absorbance ratioing at 50% peptide remaining, and kinetic analysis where ideally first order loss of parent peptide should be observed. However, when run under peudo first order conditions, the degradation of the parent peptide, A, cannot display a first order decay curve if degradation products B or C [where A→B→C], which have the same retention time and similar molar absorbtivity, build up to any appreciable extent.

Kinetic analysis was carried out by least squares analysis of log (integration peak area) versus time. When necessary, correction was made for small, interfering media peaks that coeluted with the parent peptide (subtraction of background). Most reactions were followed for at least two halflives (except for the most stable peptides) and all pseudo first order plots were linear showing correlation coefficients greater than 0.98 (8 points).

TABLE 3

| Peptide | Stability | MHC Binding Assay | | | Cellular Assay | |
|---|---|---|---|---|---|---|
| Sequence[1] | t½(min)[2] | DR1[3] | DR4w4[3] | DR4w14[4] | DR1[5] | DR4w4[5] |
| aAXAAAATLKAAa-$NH_2$ | 356 | ++ | ++ | ++ | ++ | ++ |
| yAAFAAAATAKAAa-$NH_2$ | 240 | ++ | ++ | ++ | ++ | ++ |
| aAXAAAKTAAAAa-$NH_2$ | 265 | ++ | ++ | ++ | ++ | ++ |
| yAAFAAAATLKAAa-$NH_2$ | 260 | ++ | ++ | ++ | ++ | ++ |
| yAAXAAAATLKAAa-$NH_2$ | 287 | ++ | ++ | ++ | ++ | ++ |
| yAAXAAAKTAAAAa-$NH_2$ | 411 | ++ | ++ | ++ | ++ | ++ |
| Ac-yAAFAAAKTLAAAa-$NH_2$ | 300 | + | ++ | ++ | ++ | ++ |
| aAFAAAATLKAAa-$NH_2$ | 445 | ++ | ++ | ++ | ++ | ++ |
| Ac-yAAXAAAKTAAAAa-$NH_2$ | n.d. | ++ | ++ | ++ | ++ | ++ |
| aXAAAKTAAAAa-$NH_2$ | 383 | ++ | ++ | ++ | ++ | ++ |
| aAFAAAKTAAAAa-$NH_2$ | 750 | ++ | ++ | ++ | ++ | ++ |
| yAAFAAAKTAAAAa-OH | 531 | ++ | ++ | ++ | ++ | ++ |
| aAFAAAATAKAAa-$NH_2$ | 335 | ++ | ++ | ++ | ++ | ++ |
| aAFAAAKTLAAAa-$NH_2$ | 495 | ++ | ++ | ++ | ++ | ++ |
| aAFAKAATAKAAa-$NH_2$ | 575 | ++ | ++ | ++ | ++ | ++ |
| aAFAAAATLKAAa-OH | 246 | ++ | ++ | ++ | + | ++ |
| Ac-aAFAAAKTAAAFa-$NH_2$ | 627 | ++ | ++ | ++ | ++ | ++ |
| Ac-aAXAAAATLKAAa-$NH_2$ | 314 | ++ | ++ | ++ | ++ | ++ |
| Ac-aAXAAAKTAAAAa-$NH_2$ | 575 | + | ++ | ++ | ++ | ++ |
| aAFAKAATLKAAa-$NH_2$ | 531 | ++ | ++ | ++ | ++ | ++ |
| aAFAAAATAKAAa-OH | 329 | ++ | ++ | ++ | ++ | + |
| yAAXAAAATKAAAa-$NH_2$ | 265 | ++ | ++ | ++ | ++ | ++ |
| Ac-yAAXAAAATLKAAa-$NH_2$ | n.d. | ++ | ++ | ++ | ++ | + |
| yAAXAAAABKAAAa-$NH_2$ | 300 | ++ | ++ | ++ | + | ++ |
| aAFAAAKTAAAFa-$NH_2$ | 665 | ++ | ++ | ++ | ++ | ++ |

TABLE 3-continued

| Peptide | Stability | MHC Binding Assay | | | Cellular Assay | |
|---|---|---|---|---|---|---|
| Sequence[1] | t½(min)[2] | DR1[3] | DR4w4[3] | DR4w14[4] | DR1[5] | DR4w4[5] |
| yAAFAAAKTAAAFa-$NH_2$ | 300 | ++ | ++ | ++ | + | ++ |
| aAXAAAABKAAAa-$NH_2$ | 216 | ++ | ++ | ++ | ++ | ++ |
| yAAFAAAKTLAAAa-$NH_2$ | 226 | ++ | ++ | ++ | + | ++ |
| aAFAAAKTAAAAa-$NH_2$ | 687 | ++ | ++ | ++ | + | ++ |
| Ac-yAAFAAAKTAAAAa-OH | 406 | ± | ++ | ++ | + | + |
| Ac-yAAFAAAATAKAAa-$NH_2$ | n.d. | ± | ++ | ± | + | + |
| Ac-yAAFAAAKTAAAFa-$NH_2$ | n.d. | + | ++ | ++ | + | + |
| Ac-yARFQRQTTLKAAa-OH | 400 | + | ++ | ++ | + | ++ |
| yAAFQRQTTLKAAa-OH | 252 | ++ | ++ | ++ | + | ++ |
| Ac-yARFQSQTTLKAKt-OH | 265 | ++ | ++ | ++ | + | ++ |
| peg-YARFQSQTTLKAKT-$NH_2$ | n.d. | ± | ++ | ++ | + | ++ |
| aFAAAKTAAAAa-$NH_2$ | 560 | + | ++ | ++ | + | n.d. |
| yAAFQRQTTLKAAa-$NH_2$ | 252 | ++ | ++ | ++ | + | ++ |

[1]. -NH2 = carboxamide. -OH = carboxylic acid. X = L-Cyclohexylalanine, B = trans-4-Hydroxy-L-proline, Ac = Acetyl, peg = Tetraethylene glycol carboxylic acid monomethylether, Lower case characters designate D-aminoacids. Upper case characters designate L-aminoacids.
[2]. Peptide stabilities are reported as half-lives (minutes), determined in 25% human serum.
[3]. Binding affinity relative to HA 307–319 = 1, where affinity greater than 1.0 is "++", 0.51 to 1.0 is "+", 0.1 to 0.50 is "±", and less than 0.1 is "–". $K_D$ of HA 307–319 peptide is approximately 5.6 nM vs. DR1 and 42 nM vs. DR4w4.
[4]. Binding affinity relative to a peptide having the sequence YARFQSQTTLKQKT = 1, where affinity greater than 1.0 is "++", 0.51 to 1.0 is "+", 0.1 to 0.50 is "±", and less than 0.1 is "–". $K_D$ of this peptide is approximately 67 nM.
[5]. Inhibition of antigen presentation is reported as follows: Inhibitor/Stimulator ratio required to inhibit 50% of the T-cell proliferation response less than 20 is designated by "++", 20 ≦ I/S < 300 is designated by "+", 300 ≦ I/S < 800 is designated by "±", and I/S ≧ 800 is designated by "–".

EXAMPLE III

This example shows that the carboxy-terminal residues can be replaced by dipeptide isosteres. In the peptides below, two C-terminal alanine residues have been replaced by either piperidine-4-carboxylic acid or cis-4-aminocyclohexanecarboxylic acid. These substitutions do not dramatically alter the DR binding affinities of these peptides relative to the parent peptide. Trans-4-aminocyclohexanecarboxylic acid would be equally well tolerated.

The results are presented in Table 4, below. The binding assays were performed as described above. The binding affinity of the test peptides is presented relative to either HA 307–319 or a peptide having the sequence YARFQSQTTLKAKT, designated here as peptide No. 717.01.

TABLE 4

| Dipeptide Isosteres | | | | |
|---|---|---|---|---|
| SEQUENCE | DR1[1] | DR4w4[1] | DR4w14[2] | $t_{1/2}$ (min.) |
| aAZAAAATKAAX$_1$ | ++ | ++ | ++ | n.d. |
| aAZAAAATKAAX$_2$ | ++ | ++ | + | n.d. |

Z = L-Cyclohexylalanine
$X_1$ = Piperidine-4-carboxylic acid
$X_2$ = cis-4-Aminocyclohexane carboxylic acid
1. Binding affinity relative to HA 307–319 = 1, where affinity greater than 1.0 is "++", 0.51 to 1.0 is "+", 0.1 to 0.50 is "±", and less than 0.1 is "–". $K_D$ of HA 307–319 is approximately 5.6 nM vs. DR1 and 42 nM vs. DR4w4.
2. Binding affinity relative to a peptide having the sequence YARFQSQTTLKQKT = 1, where affinity greater than 1.0 is "++", 0.51 to 1.0 is "+", 0.1 to 0.50 is "±", and leso than 0.1 is "–". $K_D$ of this peptide is approximately 67 nM.

EXAMPLE IV

This example shows that incorporation of reduced amino acid residues (amino alcohols) at the C- terminus of DR binding peptides does not adversely affect their binding affinities (Table 5).

The binding assays were performed as described above. The binding affinity of the test peptides is presented relative to either HA 307–319 or a peptide having the sequence YARFQSQTTLKAKT, designated here as peptide No. 717.01.

TABLE 5

| Peptides with Reducers Carboxy Termini | | | |
|---|---|---|---|
| SEQUENCE | DR1[1] | R4w4[1] | R4w14[2] |
| yAKFAAAKTAAAAB | + | ++ | ++ |
| yAFQRQTTLKAAB | + | ++ | ++ |

B = L-Threoninol
1. Binding affinity relative to HA 307–319 = 1, where affinity greater than 1.0 is "++", 0.51 to 1.0 is "+", 0.1 to 0.50 is "±", and less than 0.1 is "–". $K_D$ of HA 307–319 is approximately 5.6 nM vs. DR1 and 42 nM vs. DR4w4.
2. Binding affinity relative to a peptide having the sequence YARFQSQTTLKQKT = 1, where affinity greater than 1.0 is "++", 0.51 to 1.0 is "+", 0.1 to 0.50 is "±", and less than 0.1 is "–". $K_D$ of this peptide is approximately 67 nM.

EXAMPLE V

This example shows that residues of MHC binding peptides can be replaced by hydrophobic amino acid mimetics without affecting binding (Table 6).

TABLE 6

| Peptides Terminated in Hydrophobic Amino acid Isosteres | | | | |
|---|---|---|---|---|
| SEQUENCE | DR1[1] | DR4w4 | DR4w14[2] | t½ (min.) |
| $X_1$AAAKTAAAFa | ++ | ++ | ++ | n.d. |
| $X_2$AAAKTAAAFa | ++ | ++ | ++ | n.d. |
| $X_3$AAAKTAAAFa | ++ | ++ | ++ | n.d. |

TABLE 6-continued

Peptides Terminated in Hydrophobic Amino acid Isosteres

| SEQUENCE | DR1[1] | DR4w4 | DR4w14[2] | t½ (min.) |
|---|---|---|---|---|
| $X_4$AAAKTAAAFa | + | ++ | ++ | 432 |
| $X_5$AAAKTAAAFa | + | ++ | ++ | n.d. |
| $X_6$AAAKTAAAFa | + | ++ | + | n.d. |
| $X_7$AAAKTAAAFa | ± | ++ | ++ | n.d. |
| $X_8$AAAKTAAAFa | − | ++ | ++ | n.d. |

$X_1$ = 3-cyclohexanepropionic acid
$X_2$ = L-adamantyl alanine
$X_3$ = L-cyclohexylalanine
$X_4$ = Adamantaneacetic acid
$X_5$ = 3-phenylpropionic acid
$X_6$ = D-adamantyl alanine
$X_7$ = 2-naphthoic acid
$X_8$ = 1-naphthoic acid 1. Binding affinity relative to peptide HA 307-319 = 1, where affinity greater than 1.0 is "++", 0.51 to 1.0 is "+", 0.1 to 0.50 is "±", and less than 0.1 is "–". $K_D$ of HA 307-319 is approximately 5.6 nM vs. DR1 and 42 nM vs. DR4w4.
2. Binding affinity relative to a peptide having the sequence YARFQSQTTLKQKT = 1, where affinity greater than 1.0 is "++", 0.51 to 1.0 is "+", 0.1 to 0.50 is "±", and less than 0.1, is "–". $K_D$ of this peptide is approximately 67 nM.

Although the foregoing invention has been described in some detail by way of illustration and example for purposes of clarity of understanding, it will be apparent that certain changes and modifications may be practiced within the scope of the appended claims.

What is claimed is:

1. A composition comprising a peptide which binds to an HLA-DR molecule and is capable of inhibiting HLA-DR restricted T cell activation, the peptide comprising, in a direction from the N- to C- terminus:

$R_1$—$R_2$—$R_3$—$R_4$—$R_5$ wherein, $R_1$ is a spacer sequence of from 2 to about 3 amino acid residues and the first amino acid of $R_1$ is y, f, or a;

$R_2$ is F, Y or cyclohexylalanine or adamantylalanine;

$R_3$ is QSQT, QRQT, ARAT, AAAT, AAAA, AAAR, AAAK AKAA, QRQ or AAA;

$R_4$ is T; and $R_5$ is AAAAa, KAAAa, LKLAt, LKAAa, AKAAa, LKAKt, or LkAAa.

2. A composition of claim 1 wherein the N-terminal residue is modified.

3. A composition of claim 2 wherein the N-terminal residue is acetylated.

4. A composition of claim 1 wherein the C-terminal residue is modified.

5. A composition of claim 4 wherein the C-terminal residue is amidated.

6. A composition of claim 1 wherein the HLA-DR molecule is DR1, DR4w4, or DR4w14.

7. A pharmaceutical composition comprising a peptide composition of claim 1.

8. A pharmaceutical composition comprising a suitable carrier and a peptide capable of binding to an HLA-DR molecule and inhibiting HLA-DR restricted T cell activation, wherein the peptide, in a direction from the N- to C- terminus, is selected from the group consisting of:

yAAXAAAATLKAAa-$NH_2$;
aAFAAAATAKAAa-NH2;
yAAFQRQTTLKAAa-$NH_2$;
yARFQSQTTLKAKt-$NH_2$; and,
yArFQRQTTLkAAa-$NH_2$ wherein X is cyclohexylalanine and —$NH_2$ is carboxamide.

9. A composition comprising a peptide which binds to an HLA-DR molecule and is capable of inhibiting HLA-DR T cell activation, wherein the peptide is selected from the group consisting of XAAAKTAAFa, XAAAKTAAAa, XAAAATKAAa, XAAAKTAA$X_1$, XAAAKTAA$X_2$, XAAAATKA$X_1$, and XAAAATKA$X_2$, wherein X is an adamantylacetyl or 3-cyclohexanepropionyl moiety, $X_1$ is piperidine-4-carboxylic acid and $X_2$ is cis- or trans-4-aminocyclohexanecarboxylic acid.

10. A pharmaceutical composition comprising a pharmaceutically acceptable carrier and the peptide of claim 9.

11. A composition comprising a peptide specifically recognized by an HLA-DR molecule having the sequence from the N- to the C- terminus:

XAAAKTAAAFa wherein X is an N-terminal hydrophobic moiety selected from the group consisting of 3-cyclohexanepropionic acid, L-adamantylalanine, L-cyclohexylalanine, adamantaneacetic acid, 3-phenylpropionic acid, D-adamantylalanine, and 2-naphthoic acid.

12. A pharmaceutical composition comprising a pharmaceutically acceptable carrier and the peptide of claim 1.

13. The composition of claim 1, wherein the peptide is selected from the group consisting of:

yAAXAAAATLKAAa-$NH_2$;
aAFAAAATAKAAa-NH2;
yAAFQRQTTLKAAa-$NH_2$;
yARFQSQTTLKAKt-$NH_2$; and,
yArFQRQTTLkAAa-$NH_2$ wherein X is cyclohexylalanine and —$NH_2$ is carboxamide.

14. The composition of claim 1, wherein the peptide, in a direction from the N- to C- terminus, is selected from the group consisting of: aAXAAAATLKAAa-$NH_2$, yAAFAAAATAKAAa-NH2, yAAFAAAATLKAAa-$NH_2$, yAAXAAAKTAAAAa-$NH_2$, Ac-yAAFAAAKTLAAAa-$NH_2$, aAFAAAATLKAAa-$NH_2$, Ac-yAAXAAAKTAAAAa-$NH_2$, aXAAAKTAAAAa-$NH_2$, aAFAAAKTAAAAa-$NH_2$, yAAFAAAKTAAAAa-OH, aAFAAAKTLAAAa-$NH_2$, aAFAKAATAKAAa-$NH_2$, aAFAAAATLKAAa-OH, Ac-aAFAAAKTAAAFa-$NH_2$, Ac-aAXAAAATLKAAa-$NH_2$, Ac-aAXAAAKTAAAAa-$NH_2$, aAFAKAATLKAAa-$NH_2$, aAFAAAATAKAAa-OH, yAAXAAAATKAAAa-$NH_2$, Ac-yAAXAAAATLKAAa-$NH_2$, yAAXAAAABKAAAa-$NH_2$, aAFAAAKTAAAFa-$NH_2$, yAAFAAAKTAAAFa-$NH_2$, aAXAAAABKAAAa-$NH_2$, yAAFAAAKTLAAAa-$NH_2$, aAFAAAKTAAAAa-$NH_2$, Ac-yAAFAAAKTAAAAa-OH, Ac-yAAFAAAATAKAAa-$NH_2$, Ac-yAAFAAAKTAAAFa-$NH_2$, Ac-yARFQRQTTLKAAa-OH, yAAFQRQTTLKAAa-OH, Ac-yARFQSQTTLKAKt-OH, peg-YARFQSQTTLKAKT-$NH_2$, and aFAAAKTAAAAa-$NH_2$; wherein —$NH_2$ is carboxamide, —OH is carboxylic acid, X is L-cyclohexylalanine, B is trans-4-Hydroxy-L-proline, Ac is acetyl, and peg is tetraethylene glycol carboxylic acid monomethylether.

15. A composition comprising a peptide which binds to an HLA-DR molecule and is capable of inhibiting HLA-DR restricted T cell activation, wherein the peptide, in a direction from the N- to C- terminus, is aAXAAAKTAAAAa-$NH_2$, wherein —$NH_2$ is carboxamide, and X is L-cyclohexylalanine.

16. A pharmaceutical composition comprising a pharmaceutically acceptable carrier and the peptide composition of claim 14.

17. A pharmaceutical composition comprising a pharmaceutically acceptable carrier and the peptide composition of claim 15.

* * * * *